US00RE49455E

(19) United States
(12) Reissued Patent
Nicholas et al.

(10) Patent Number: US RE49,455 E
(45) Date of Reissued Patent: Mar. 14, 2023

(54) SURGICAL STAPLING DEVICE WITH CAPTIVE ANVIL

(71) Applicant: Covidien LP, Mansfield, MA (US)

(72) Inventors: David A. Nicholas, Trumbull, CT (US); Peter T. Datcuk, Glenside, PA (US); Michael P. Whitman, New Hope, PA (US)

(73) Assignee: COVIDIEN LP, Mansfield, MA (US)

(21) Appl. No.: 17/161,912

(22) Filed: Jan. 29, 2021

Related U.S. Patent Documents

Reissue of:
(64) Patent No.: 8,235,272
Issued: Aug. 7, 2012
Appl. No.: 12/622,862
Filed: Nov. 20, 2009

(51) Int. Cl.

| | |
|---|---|
| ***A61B 17/068*** | (2006.01) |
| ***A61B 17/072*** | (2006.01) |
| *A61B 17/00* | (2006.01) |
| *A61B 17/29* | (2006.01) |

(52) U.S. Cl.
CPC ..... *A61B 17/068* (2013.01); *A61B 17/07207* (2013.01); *A61B 17/00234* (2013.01); *A61B 2017/00734* (2013.01); *A61B 2017/07214* (2013.01); *A61B 2017/2926* (2013.01); *A61B 2017/2943* (2013.01)

(58) Field of Classification Search
CPC ..... A61B 17/068; A61B 17/07207; A61B 17/00234; A61B 2017/00734; A61B 2017/07214; A61B 2017/2926; A61B 2017/2943
See application file for complete search history.

(56) References Cited

U.S. PATENT DOCUMENTS

| | | | | |
|---|---|---|---|---|
| 5,307,976 | A * | 5/1994 | Olson et al. | 227/175.3 |
| 5,433,721 | A * | 7/1995 | Hooven et al. | 606/143 |
| 5,485,952 | A * | 1/1996 | Fontayne | 227/178.1 |
| 5,540,375 | A * | 7/1996 | Bolanos et al. | 227/178.1 |
| 5,814,055 | A | 9/1998 | Knodel et al. | |
| 5,820,009 | A * | 10/1998 | Melling et al. | 227/176.1 |
| 6,079,606 | A * | 6/2000 | Milliman et al. | 227/175.2 |
| 6,830,174 | B2 | 12/2004 | Hillstead et al. | |
| 7,464,849 | B2 * | 12/2008 | Shelton et al. | 227/178.1 |
| 7,588,177 | B2 * | 9/2009 | Racenet | 227/181.1 |
| 7,617,961 | B2 * | 11/2009 | Viola | 227/175.1 |
| 2007/0023477 | A1 | 2/2007 | Whitman et al. | |
| 2009/0095790 | A1 | 4/2009 | Whitman et al. | |
| 2009/0101692 | A1 | 4/2009 | Whitman et al. | |
| 2009/0182193 | A1 | 7/2009 | Whitman et al. | |

* cited by examiner

*Primary Examiner* — Catherine S Williams
(74) *Attorney, Agent, or Firm* — Carter, Deluca & Farrell, LLP

(57) ABSTRACT

A device for clamping tissue includes a first jaw having a distal portion for communicating with tissue and a proximal portion having a first wing and a second wing. The device also includes a second jaw having a distal portion for communicating with tissue and a proximal portion having a first slot and a second slot, the first slot disposed between a middle structure and a first lateral structure, the second slot disposed between the middle structure and a second lateral structure. The first jaw is rotatably coupleable to the second jaw with the first wing extending into the first slot and the second wing extending into the second slot.

20 Claims, 15 Drawing Sheets

SURGICAL STAPLING DEVICE WITH CAPTIVE ANVIL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates generally to a surgical clamping device.

BACKGROUND INFORMATION

Some surgical procedures require the compression, e.g., clamping, of a patient's tissue. Such procedures may include, e.g., anastomosing, stapling, and resecting of tissue. For example, where cancerous tissue is identified in a patient's gastrointestinal tract, the cancerous tissue may need to be surgically removed. Where, for example, the cancerous tissue is located on the colon and is accessible by surgical instrumentation, the surgeon may make an incision in the patient's abdomen to allow access to the bowel. The surgeon may then use a linear cutting and stapling device, such as that described in U.S. Patent Application Publication No. 2009/0101692, which is expressly incorporated herein in its entirety by reference thereto, to cut and staple the colon tissue on opposite sides of the cancerous portion to be removed. In this procedure, the colon is externally clamped (e.g., between opposed jaws) to compress the tissue. While the tissue is compressed, a cutter and a stapler are activated to make a linear cut and apply typically two linear rows of staples in the areas adjacent the cut.

The stapling thus closes both open ends of the portion of the bowel to be removed, as well as providing a temporary closure of the two cut ends of the bowel. This closure limits exposure of the surrounding tissue to the interior of the bowel, thus limiting the risk of infection.

After the cutting and stapling procedure, the cancerous portion of tissue may be removed from the patient's body.

To achieve effective stapling, e.g., in the above procedures, the tissue must be compressed to the extent that there is an adequately small tissue gap, e.g., one millimeter, between the faces of the tool. During this compression, the mechanical components of the clamping mechanism of the cutting and stapling device may be subjected to a high level of force or strain. Where, e.g., the jaws are closed by rotation of one or both of the jaws about a proximally located pin, the pin and/or the adjacent structures of the jaws in communication with the pin bear a substantial load, which may lead to deformation. Where the pin passes through a through hole in one or both of the jaws, deformation may be more likely due to the weakening of the jaw structure resulting from the through holes.

Further, proximally extending structures of the jaws, e.g., an anvil, may deform, including, e.g., splaying laterally outwardly. The likelihood of deformation may also be increased by the removal of material for through slots, e.g., in a pin-and-slot type actuation arrangement.

This deformation may lead to, e.g., misalignment between the jaws and/or failure of the clamping mechanism. Where one of the jaws is configured as an anvil and the other jaw is configured to drive staples, e.g., from a staple cartridge, into the anvil, misalignment of the jaws may cause misalignment of the anvil and staple pockets. This may cause the staples to be improperly formed, which may increase the risk of sepsis and other potentially dangerous complications.

Thus, it is desirable to provide a clamping mechanism that substantially reduces the likelihood of deformation in the jaws.

SUMMARY

Example embodiments of the present invention provide a high-strength anvil and housing while maintaining accurate anvil to staple pocket positioning. This may be accomplished by integrating the pivot point into the anvil and housing geometry rather than using a separate pivot pin. This design may be advantageous in that the integrity of the anvil and housing is not compromised by the need to drill a through hole for a pin. In this regard, a portion of material (which would otherwise be removed due to drilling of a through hole) remains in the region of the pivot point to assist in supporting the significant loads exerted during the compression of tissue. This may result in increased clamping force with less deflection in the anvil and/or the housing.

Accurate distal to proximal anvil positioning may be accomplished by providing the anvil and cartridge housing with mating geometry, e.g., mating cylindrical surfaces. For example, the anvil or the cartridge housing may have a concave cylindrical surface that receives a convex cylindrical surface (which may have the same, or substantially the same, radius of curvature) of the other of the anvil or the cartridge housing. It should be understood that the device may have multiple mating interfaces and that one of the anvil and the cartridge housing may have a combination of convex and concave geometries that mate with a corresponding combination of concave and convex geometries on the other of the anvil and the cartridge housing.

When the mating surfaces of the anvil and the cartridge housing are mated and clamping force is exerted between the anvil and the cartridge housing, the mated surfaces of the anvil and the cartridge housing accurately locate, or position, the anvil. In this regard, the example device is configured such that applying a load to the anvil during clamping causes the mating surfaces to be pressed toward each other, thereby maintaining the mated arrangement. In the absence of a load being applied to the anvil, or when the mated surfaces are not being pressed together, the position of the anvil is maintained by a secondary positioning member, e.g., a secondary pin or screw, which may, e.g., be supported by the housing and received by the anvil, e.g., in a slot of a wing of the anvil. Where the secondary positioning member is received in a slot, the slot may be a blind slot as opposed to a through slot, to avoid potential weakening of the structure. It should be appreciated that the secondary positioning member may be supported in either of the anvil and the cartridge housing. Further, a plurality of secondary positioning members may be provided such that either or both of the anvil and the cartridge housing support the positioning members.

According to an example embodiment, the anvil and cartridge housing are configured so that the anvil is generally laterally confined in a particular arrangement by the cartridge housing. This is accomplished by one or more structures of the anvil being receivable in a slot or space formed in the cartridge housing. For example, two wings of the anvil may be received in two corresponding slots of the cartridge housing. This slot configuration allows the presence of the cartridge housing structure around a relatively high portion of the circumference of the cartridge housing, which may be advantageous with regard to the strength of the cartridge housing.

The slotted arrangement may also be advantageous with regard to the anvil, since the structure of the cartridge housing extends on laterally outward sides of the wings and between the wings when the anvil is mated to the cartridge housing. This may, e.g., decrease the likelihood of lateral deflection of the wings.

The anvil of the example embodiment also has a cam slot for actuation of the anvil that does not extend laterally through the anvil. This blind slot may increase the strength of the anvil due to the presence of more structure on the outer surface as opposed to a through slot.

According to an example embodiment of the present invention, a device for clamping tissue includes a first jaw having a distal portion for communicating with tissue and a proximal portion having a first wing and a second wing. The device also includes a second jaw having a distal portion for communicating with tissue and a proximal portion having a first slot and a second slot, the first slot disposed between a middle structure and a first lateral structure, the second slot disposed between the middle structure and a second lateral structure. The first jaw is rotatably coupleable to the second jaw with the first wing extending into the first slot and the second wing extending into the second slot.

The first wing may include a first blind slot and the second wing may include a second blind slot, the first and second blind slots configured to receive opposite ends of an actuation shaft.

The middle structure of the second jaw may include a slot configured to receive a middle portion of the actuation shaft when the ends of the actuation shaft are received in the blind slots of the first and second wings.

The first jaw may include a first bearing surface formed monolithically with the first jaw and the second jaw may include a second bearing surface formed monolithically with the second jaw, the first bearing surface communicating with the second bearing surface to define an axis of rotation between the first jaw and the second jaw when the first jaw is rotatably coupled to the second jaw.

The first and second bearing surfaces may have curvatures that maintain an axial position of the first jaw with respect to the second jaw when a clamping force is applied between the first jaw and the second jaw.

The device may also include a secondary positioning member coupled to one of the first jaw and the second jaw and configured to prevent removal of the first jaw from the second jaw and to allow rotation of the first jaw with respect to the second jaw.

The secondary positioning member may be at least one of a pin and a screw.

The secondary positioning member may be configured to extend from the one of the first jaw and the second jaw into a curved slot of the other one of the first jaw and the second jaw.

The curved slot may be a blind slot.

The first jaw may be an anvil and the second jaw may be a staple cartridge housing configured to drive staples into the anvil when the anvil is in a closed position.

According to an example embodiment of the present invention, a device for clamping tissue includes a first jaw having a first jaw body having a proximal portion and a distal clamping portion, and a first bearing surface formed monolithically with the first jaw body as a single piece. The device also includes a second jaw having a second jaw body having a proximal portion and a distal clamping portion, and a second bearing surface formed monolithically with the second jaw body. The second jaw is rotatably coupleable to the first jaw such that the first bearing surface communicates with the second bearing surface at an interface. The device also includes a driver configured to rotate the first jaw with respect to the second jaw with the interface acting as a fulcrum and defining an axis of rotation between the first jaw and the second jaw.

The first bearing surface and the second bearing surface may be configured to slide with respect to each other along the interface when the driver rotates the first jaw with respect to the second jaw.

The interface may extend along a circular arc, the first jaw rotatable with respect to the second jaw about an axis of rotation corresponding to the circle center of the circular arc.

The first bearing surface may be formed in the first jaw without extending entirely through the first jaw and the second bearing surface may be formed in the second jaw without extending entirely through the second jaw.

The first jaw may include a first wing and a second wing, the first wing including a first blind slot and the second wing including a second blind slot.

The driver may include a shaft configured to extend into each of the first blind slot and the second blind slot.

The shaft may be actuatable along a slot in the second jaw to rotate the first jaw with respect to the second jaw.

The shaft may be disposed proximally with respect to the interface between the first bearing surface and the second bearing surface.

The first jaw may be axially insertable and removable from the second jaw when no clamping force is applied between the first jaw and the second jaw.

The device may further include a secondary positioning member coupled to one of the first jaw and the second jaw and configured to prevent axial removal of the first jaw from the second jaw and to permit rotation of the first jaw with respect to the second jaw.

The secondary positioning member may be configured to limit the range of rotation between the first jaw and the second jaw to a predetermined angular range.

The secondary positioning member may be configured to extend from the one of the first jaw and the second jaw into a curved slot of the other one of the first jaw and the second jaw.

The curved slot may be a blind slot.

Further details and aspects of example embodiments of the present invention are described in more detail below with reference to the appended figures.

DETAILED DESCRIPTION

Figure 1A:
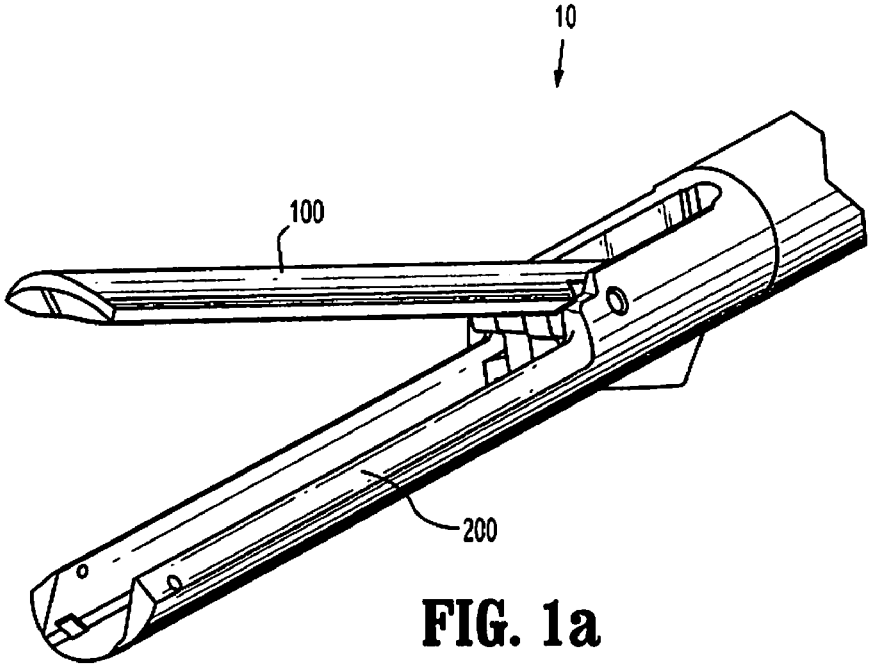
FIGS. 1a and 1b show a clamping device according to an example embodiment of the present invention.
Figure 1B:
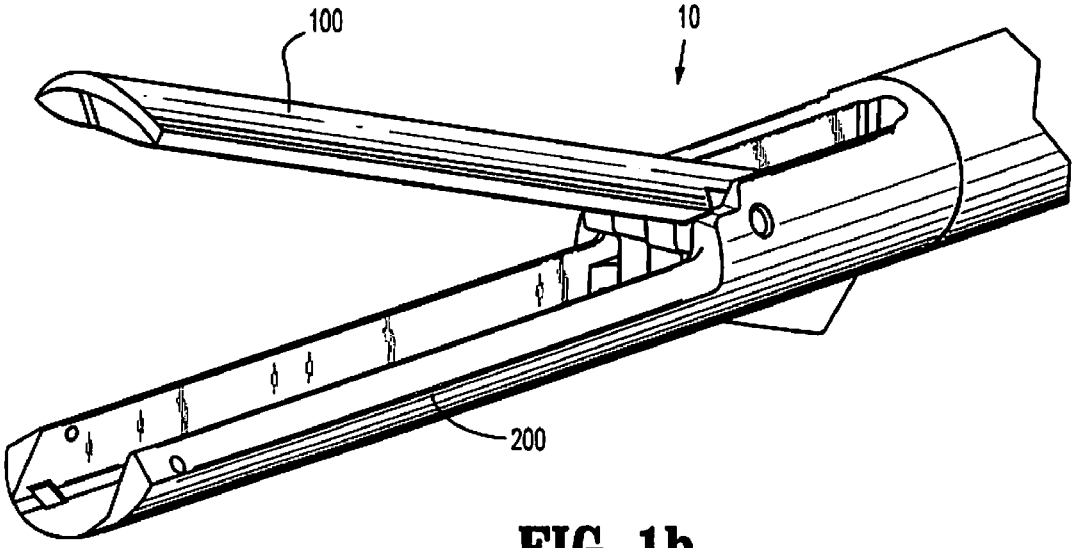

FIGS. 1a and 1b show a clamping device 10 of a linear cutting and stapling device according to an example embodiment of the present invention. The clamping device 10 includes an anvil 100 as a first jaw or clamping member, and a cartridge housing 200 as a second jaw clamping member. As shown in FIGS. 1a and 1b, the anvil 100 and the cartridge housing 200 are in an open state. The anvil 100 and cartridge housing 200 are rotatable about each other to close from the open state to a closed state where the anvil 100 and cartridge housing 200 are parallel, or substantially parallel, to maintain a tissue gap therebetween that allows for satisfactory staple formation between the cartridge housing 200 and the anvil 100.

It is noted that the clamping device 10 is symmetric, or substantially symmetric, about a plane extending through an axial centerline of the clamping device 10. Thus, although some features may be described with respect to one side of the clamping device, it should be understood than analogous features are disposed on the opposite side of the clamping device. It should be further understood that, although the clamping device 10 is symmetric, or substantially symmetric, other example embodiments may not be.

Figure 2:
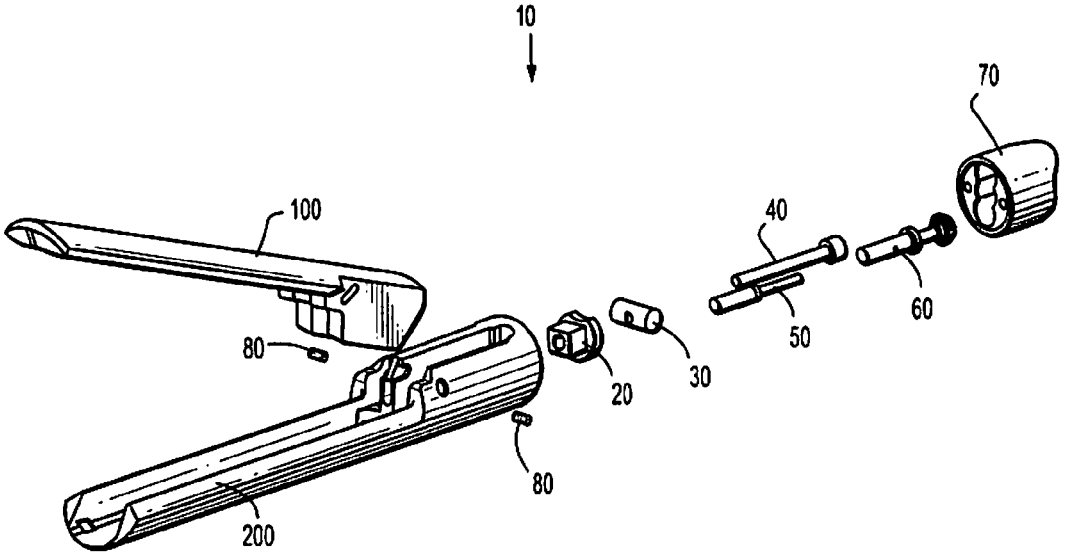
FIG. 2 is an exploded view of the clamping device.

FIG. 2 is an exploded view of the clamping device 10 of FIGS. 1a and 1b. The clamping device 10 includes a guide screw or member 20, an inner shaft 30, a clamp screw 40, a firing shaft 50, a bevel gear shaft 60, a proximal housing 70, and screws 80.

Figure 3:
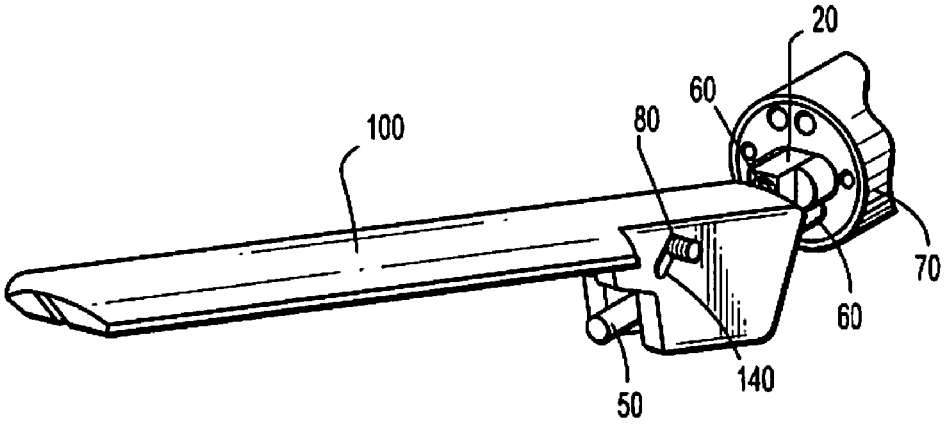
FIG. 3 shows components of the clamping device.
Figure 4:
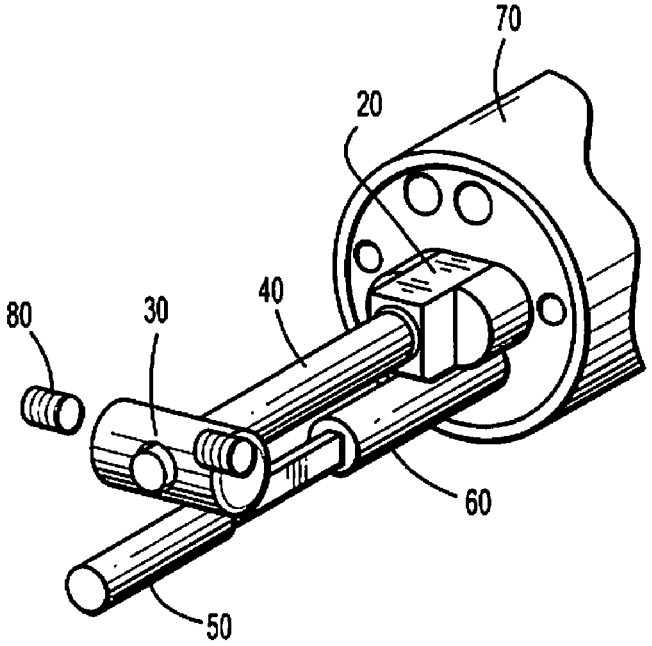
FIG. 4 shows components of the clamping device.
Figure 5A:
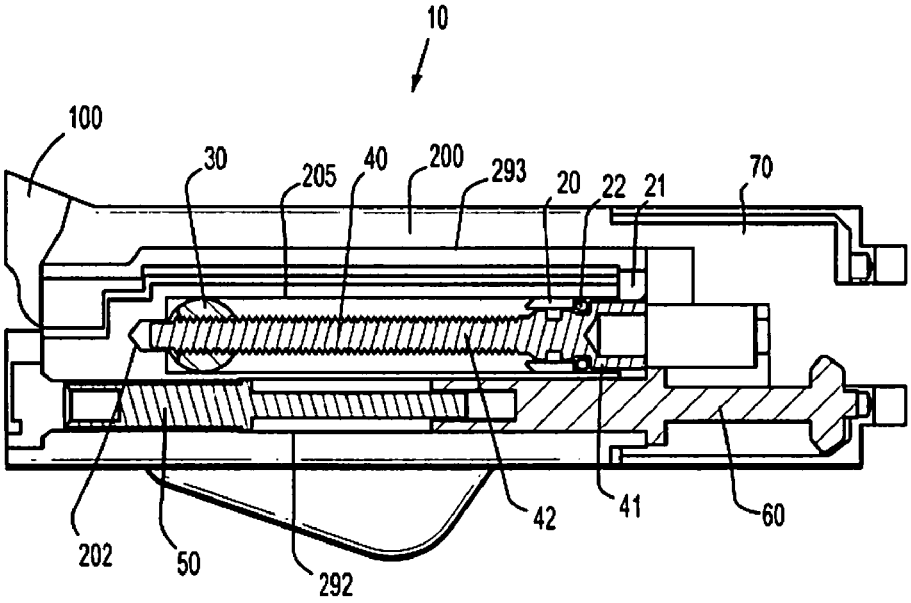
FIGS. 5a to 5c show cross-sectional views of a proximal portion of the clamping device.
Figure 5B:
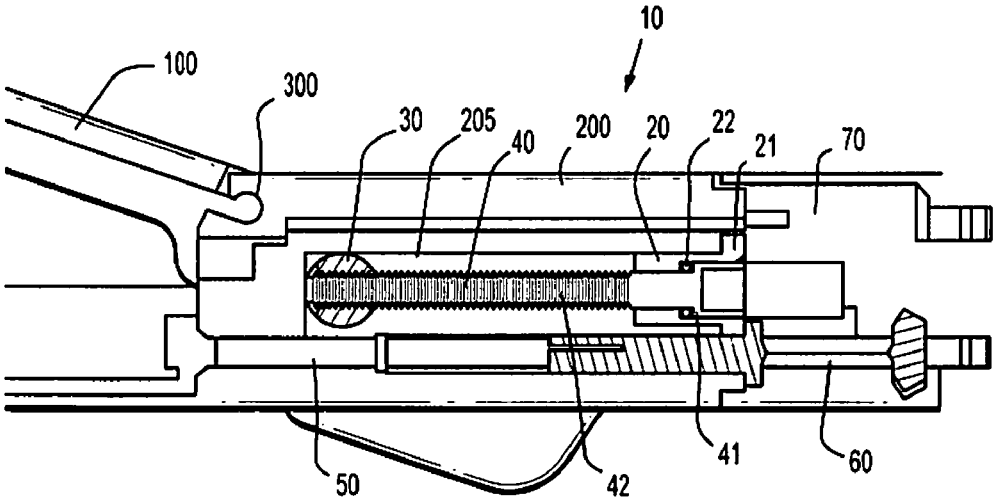

Referring to FIGS. 3 and 4, the guide member 20 is coupled to the proximal housing 70 and rotatably receives the clamp screw 40. Further referring to FIGS. 5a and 5b (FIG. 5a is a cross section taken through a plane crossing the mid- or centerline of the clamping device 10, while the cross-sectional view of FIG. 5b is taken through a plane that is slightly offset from the centerline of the clamping device 10), the guide member 20 has a flange 21 that contacts the staple cartridge housing 200 to prevent the flange from moving axially in a distal direction. A proximal face of the flange 21 contacts the proximal housing to restrain the guide member from moving proximally.

The clamp screw 40 has a head or proximal portion 41 configured to receive a driver to axially rotate the clamp screw 40. The clamp screw 40 also has an externally threaded shaft 42 that engages corresponding internal threads of the inner shaft 30. In this regard, axial rotation of the clamp screw 40 in a first direction causes the external threads to rotate within the inner shaft 30 to cause the inner shaft 30 to move in a proximal direction. As set forth in greater detail below, this proximal movement is translated into a clamping force applied between the anvil 100 and the cartridge housing 200. To facilitate rotation of the clamp screw 40 during the clamping, a thrust bearing 22 is provided to transmit the axial force between the clamp screw 40 and the guide member 20 about the guide member 20. Rotation of the clamp screw 40 in a second, opposite direction causes the inner shaft 30 to move distally, causing the anvil 100 to rotate away from the cartridge housing. A distal end portion of the clamp screw 40 is received in a bore 202 of the cartridge housing 200 to constrain the distal end of the clamp screw 40 during clamping.

To drive a cutting and stapling function, the clamping device 10 includes a firing shaft 50 and a bevel gear shaft 60. The bevel gear shaft 60 is coupled to the firing shaft 50 such that rotation of the bevel gear shaft causes rotation of the firing shaft 50. This rotation of the firing shaft is then used to drive a cutting and staple-pushing element in a distal direction to cut and staple clamped tissue. The staples are driven from a staple cartridge received by the cartridge housing 200.

Figure 10:
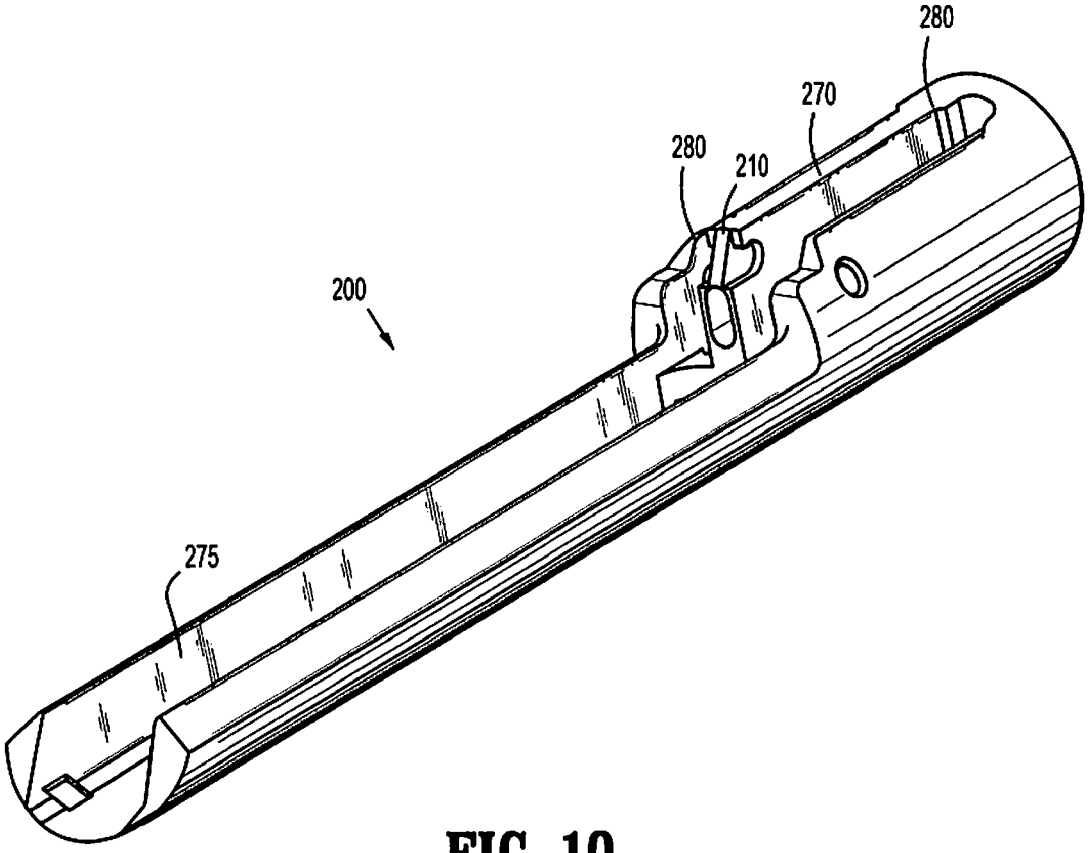
FIG. 10 shows a staple cartridge housing or jaw of the jaw portion of FIGS. 1a and 1b.
Figure 11:
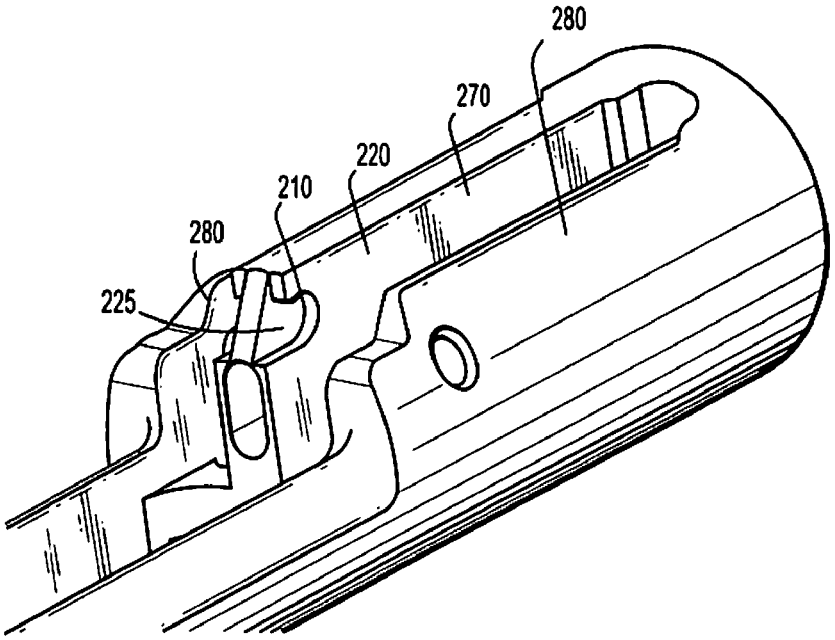
FIG. 11 shows a proximal portion of the jaw of FIG. 10.
Figure 12:
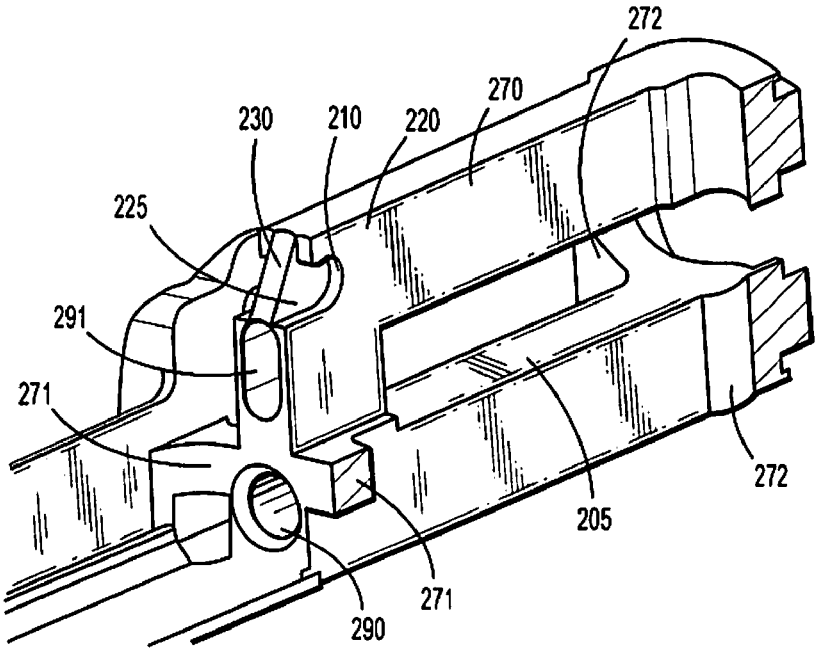
FIG. 12 shows a cross-sectional view of the proximal portion of FIG. 11.
Figure 13:
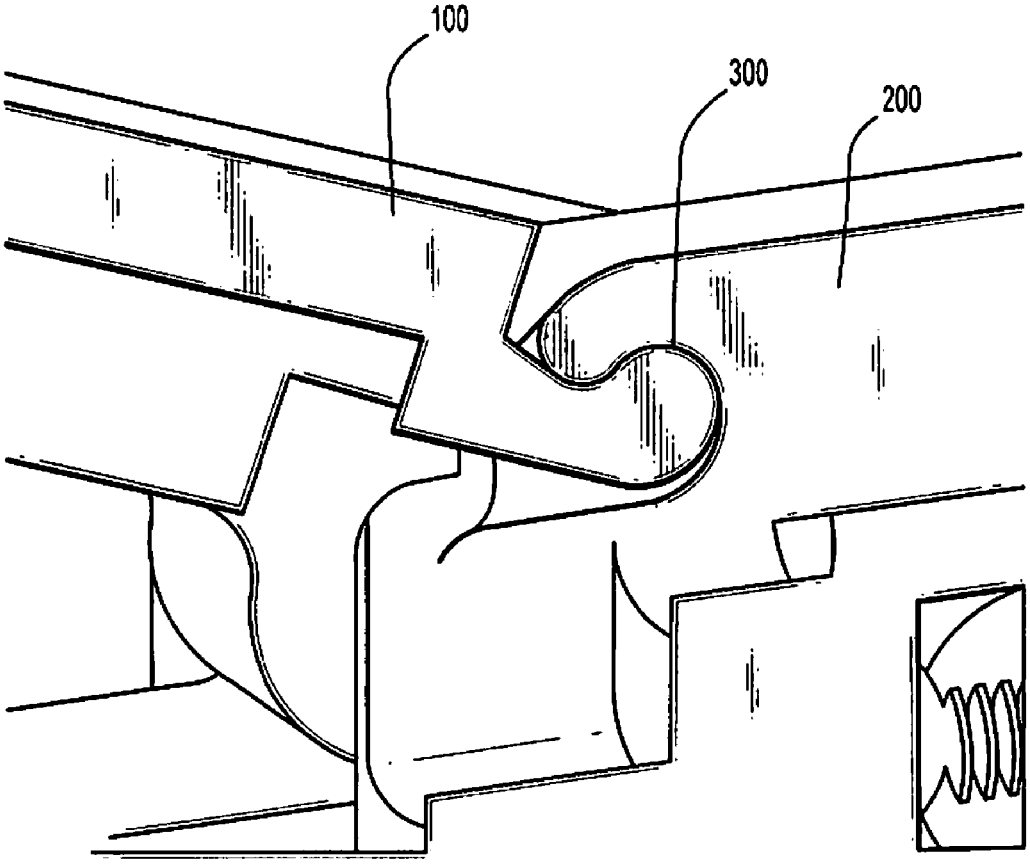
FIG. 13 shows a cross-sectional view of an interface between the anvil of FIG. 6 and the staple cartridge housing of FIG. 10.

Referring to FIG. 5b and FIG. 13, which is a cross sectional view taken through an interface 300 between the anvil 100 and the cartridge housing 200, the anvil 100 is rotatably coupled to the cartridge housing 200 at the interface 300. The interface 300 is formed between a concave surface 210 of the cartridge housing 200 and a convex surface 110 of the anvil 100. The concave surface 210 of the cartridge housing 200 is shown, e.g., in FIGS. 10 to 12, and the convex surface 110 of the anvil 100 is shown, e.g., in FIGS. 6 to 9.

The convex surface 110 of the anvil 100 corresponds to the profile of a raised portion or protrusion 115 that extends or projects away from a lateral surface or face 120 to a raised surface or face 125. Although the protrusion 115 extends inwardly (i.e., in a direction toward an axial centerline of the anvil 100) from an inwardly facing surface 120 (i.e., a surface facing laterally toward the centerline of the anvil 100), it should be understood that the protrusion 115 may extend away from an outwardly facing surface and/or the protrusion 115 may extend between two opposed surfaces.

The concave surface 210 of the cartridge housing 200 corresponds to the profile of an undercut or inset into a lateral surface or face 220. Although the inset is formed to extend inwardly from an outwardly facing surface 220, it should be understood that the inset may be formed to extend outwardly into an inwardly facing surface and/or the inset may extend through the material to an opposite face or surface.

Further, the concave surface 210 is formed at a step between the face 220 and an inset surface or face 225. The surface 225 is formed on the lateral side of a support member or rib 230. In the example embodiment, the rib 230 separates the concave surface 210 and the inset from a symmetrically formed, or substantially symmetrically formed, second concave surface and second inset. This second structure is formed as "mirror image" such that the structure is symmetric about a plane that intersects the axial centerline of the cartridge housing 200 and corresponds to a plane in which the anvil 100 is rotatable with respect to the cartridge housing 200 when the anvil 100 is mated to the cartridge housing 200 at the interface 300. It should be appreciated, however, that the support member 230 may be dispensed with, such that, e.g., the concave surface 210 extends laterally across the cartridge housing 200 to form a single surface 210. The support member 230 may be advantageous, however, in that it may help prevent deformation of the cartridge housing 200 due to high forces being exerted at the interface 300.

When the anvil 100 and the cartridge housing 200 are mated, the convex surface 110 is slidably coupled with the concave surface 210. The contact surface between the convex surface 110 forms an arc with a center corresponding to an axis of rotation between the anvil 100 and the cartridge housing 200. In this regard, the radius of curvature of the concave surface 210 and the convex surface 110 are the same, or substantially the same. This may ensure accurate positioning of anvil 100 with respect to the cartridge housing 200, as well as providing a constant, or substantially constant, axis of rotation between the anvil 100 and the cartridge housing 200 during clamping.

Although the interface 300 provides a sliding interface, it should be understood that other configurations may be provided. For example a rolling interface may be provided. For example, the concave surface 210 may have a larger radius of curvature than the convex surface 110. Where, e.g., such a rolling arrangement is provided, the concave surface 210 and the convex surface 110 may be provided with mating teeth, e.g., gear teeth, which may be formed with the respective anvil 100 and cartridge housing 200 monolithically.

Although the clamping device 10 has two mating interfaces 300 it should be understood that the clamping device 10 may have multiple mating interfaces 300 and that one of the anvil 100 and the cartridge housing 200 may have a combination of convex and concave geometries that mate with a corresponding combination of concave and convex geometries on the other of the anvil 100 and the cartridge housing 200.

Due to the geometry of the interface 300, the anvil 100 is constrained axially with respect to the cartridge housing 200 when the convex surface 110 is pressed into the concave surface, e.g., during clamping. In this regard, the contact or interface surface 300 extends from a point proximal to the rotation axis, or center of curvature of the arc of interface 300 (which corresponds to the center of curvature of the convex surface 110 and the center of curvature of the concave surface 210) to a point proximal to the center of the arc of curvature of the interface 300. Thus, the surface 210 of the cartridge housing 200 is able to exert forces (normal to the surface 210) that have proximally directed components and distally directed components, thereby accurately maintaining the axial position of the anvil 100 with respect to the cartridge housing 200.

It should be appreciated that, although the interface 300 includes a single contact or interface surface, the interface may be provided with multiple and/or intermittent contact or interface surfaces.

When the convex surface 110 is not pressed into the concave surface 210, e.g., when no clamping force is applied to the anvil 100, the surface 110 may separate from the surface 210, in which case the anvil 100 may be moved axially with respect to the cartridge housing 200 such that the surface 110 clears the surface 210. In this manner, the anvil 100 may be removed, or decoupled, from the cartridge housing 200.

When it is not desired to remove the anvil 100 from the cartridge housing 200, in the absence of a load being applied to the anvil 100, or when the mated surfaces 110, 120 are not being pressed together, the position of the anvil 100 is maintained by one or more secondary positioning members 80. The secondary positioning members 80 of the device 10 are shown as, e.g., screws. Each secondary positioning member 80 is supported by the cartridge housing 200 and extends into a secondary positioning slot 140 in the anvil 100. The secondary positioning slot 140 has an arced geometry, the center of curvature of the arc located at the axis of rotation of the anvil 100 with respect to the cartridge housing when the surfaces 110 and 210 are mated. Thus, the extension of the secondary positioning member into the secondary positioning slot 140 does not interfere with the rotational motion of the anvil 100 with respect to the cartridge housing 200 when the anvil 100 is moved between an open position and a closed position. The length and/or positioning of the arced slot may be selected, however, to limit the range of rotation of the anvil 100 when rotated about the cartridge housing. This limiting would be provided due to contact or interference between the secondary positioning member 80 and one or both of the ends of the arced secondary positioning slot 140.

The secondary positioning member 80 is a screw having external threads that engage internal threads of a secondary positioning aperture 240 of the cartridge housing 200.

Although the secondary positioning member 80 is a screw, it should be appreciated that the secondary positioning member 80 may be any appropriate structure, e.g., a pin. Moreover, although the slot 140 is a blind slot (i.e., the depth of the slot does not extend entirely through the structure of the anvil 100), a through slot may be provided. A blind slot may be advantageous, however, due to the added rigidity provided by the material at the bottom of the slot. It should be further appreciated that the secondary positioning member 80 may be supported in either of the anvil 100 and the cartridge housing 200. Further, although two secondary positioning members 80 are shown, more than two secondary positioning members 80 may be provided, or a single secondary positioning member 80 may be provided. For example, a single pin or screw could extend through both slots 140.

Figure 5C:
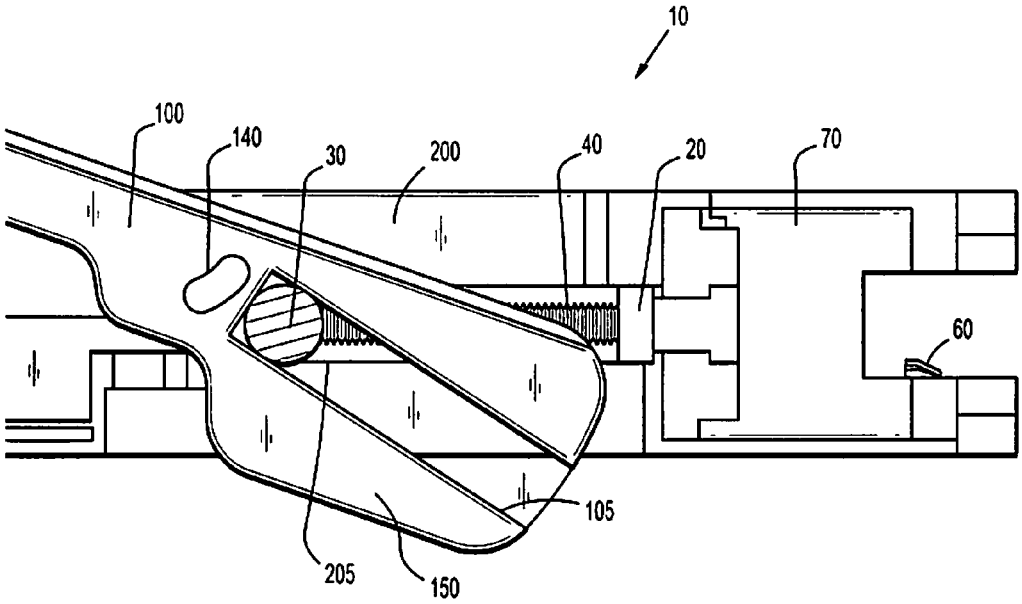
Figure 6:
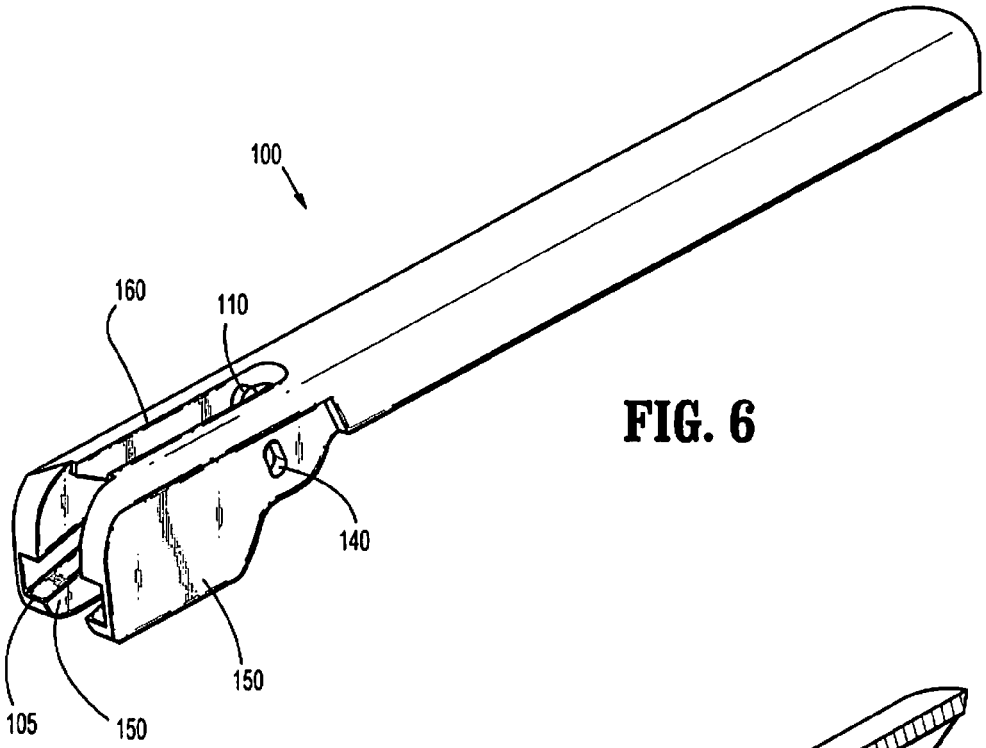
FIG. 6 shows an anvil jaw of the clamping device.
Figure 7:
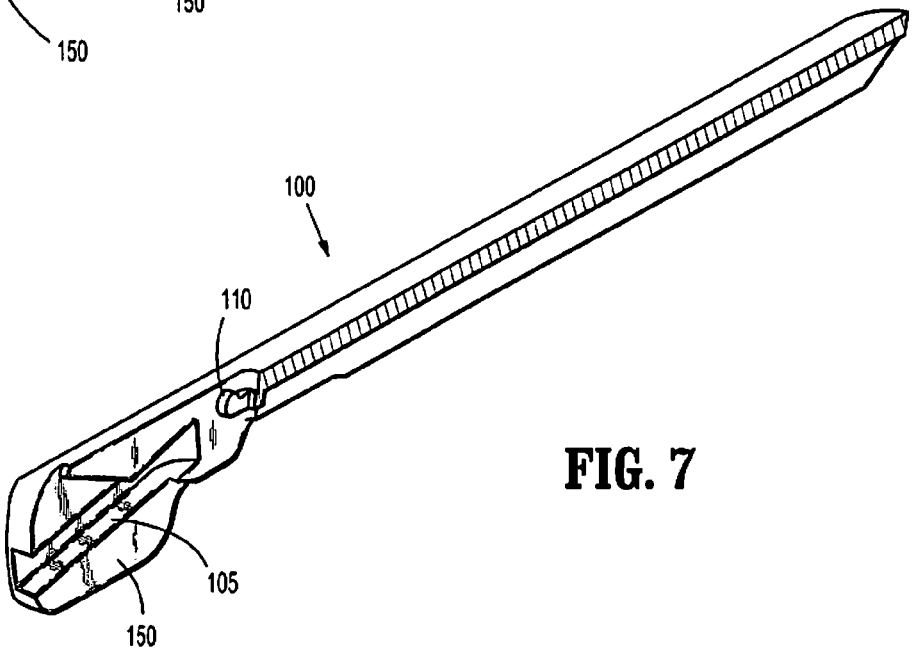
FIG. 7 shows a cross-sectional view of the anvil jaw of FIG. 6.
Figure 8:
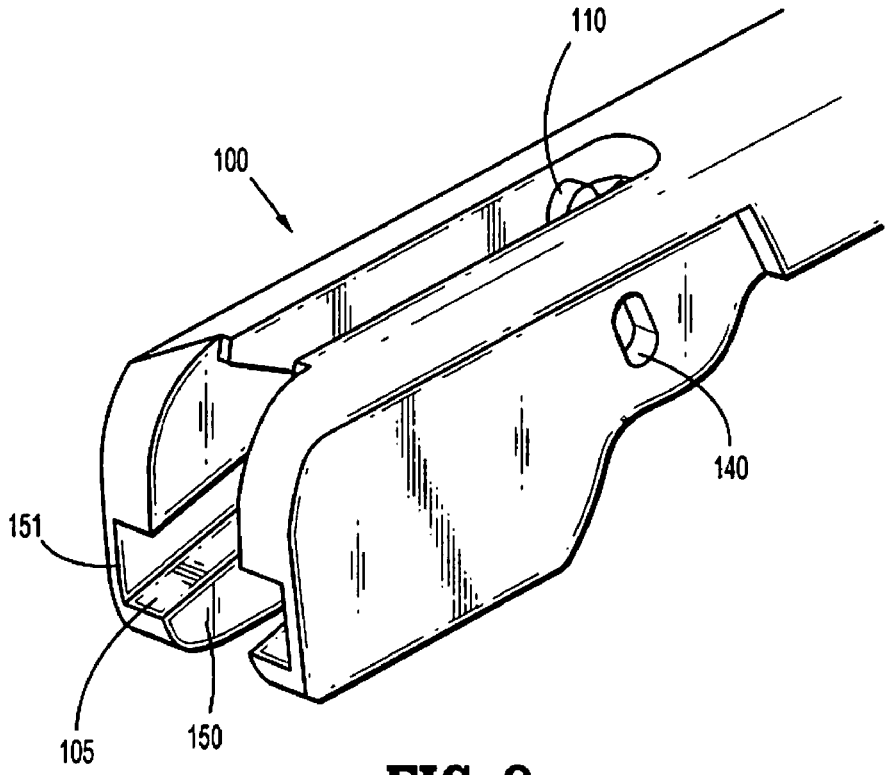
FIG. 8 shows a proximal portion of the anvil jaw of FIG. 6.
Figure 9:
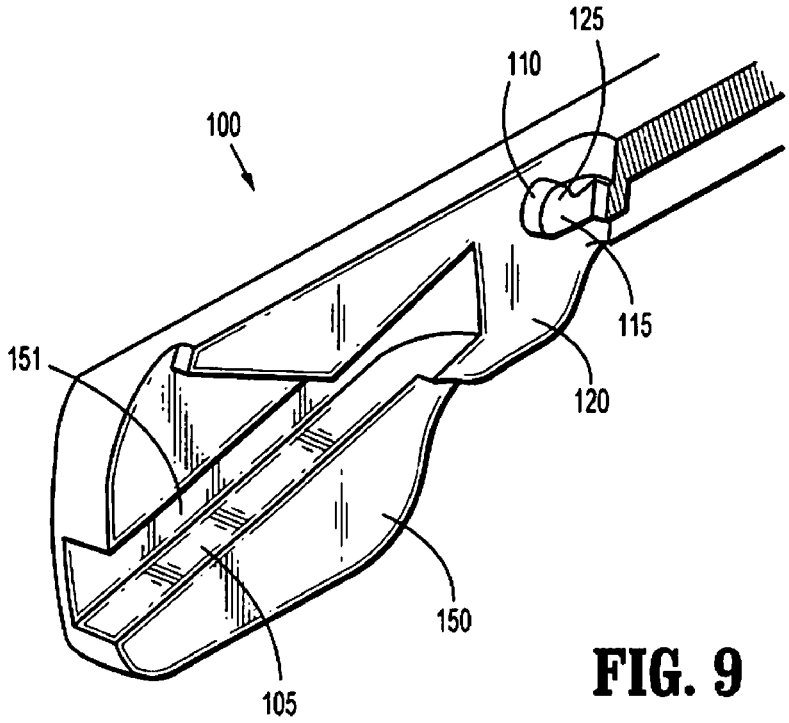
FIG. 9 shows a cross-sectional view of the proximal portion shown in FIG. 8.

Referring to FIGS. 5a to 5c, to actuate the rotation of the anvil 100, the inner shaft 30 moves proximally and distally within a slot 205 of the cartridge housing 200. The slot 205 constrains the inner shaft 30 to an axial path with respect to the cartridge housing 200. Thus, the inner shaft 30 may move distally and proximally along this path, but is limited with regard to movement in other directions in the plane of rotation of the anvil 100 about the cartridge housing 200. It should be appreciated that the path of the inner shaft 30 provided by the slot 205 need not necessarily be linear. The cartridge housing 200 may also rotationally constrain the inner shaft 30 about the axis of the clamp screw 40 with respect to the cartridge housing 200 such that rotation of the clamp screw 40 with respect to the cartridge housing 200 does not cause rotation of the inner shaft 30 about the cartridge housing 200. Thus, clamp screw 40 rotates relative to the cartridge housing 200 and the inner shaft 30, the threaded engagement between the clamp screw 40 and the inner shaft 30 causing the inner shaft 30 to translate distally or proximally depending on the direction of rotation of the clamp screw 40.

The inner shaft 30 extends laterally outwardly into actuation slots 105 of the anvil 100, such that the distal or proximal translation of the inner shaft 30 within the slot 205 of the cartridge housing 200 causes the shaft to translate, e.g., slide, along the paths of the actuation slots 105. It should be appreciated that the inner shaft 30 may be configured to roll along the slots 105 of the anvil 100 and/or along the slot 205 of the cartridge housing 200.

Each slot 105 is located and oriented such that the movement of the inner shaft 30 along the slot 205 of the cartridge housing 200 and along the actuation slot 105 of the anvil 100 causes the anvil 100 to rotate with respect to cartridge housing 200. This is accomplished by providing the slots 105 and 205 such that the distal portions of the slots 105 and 205 align when the anvil 100 is in the open position with respect to the cartridge housing 200 and the proximal portions of the slots 105 and 205 align when the anvil 100 is in a closed position with respect to the cartridge housing 200. In this regard, the inner shaft 30 serves to align the slots 105 and 205 at the position along the slots 105 and 205 at which the inner shaft 30 is located. Thus, when the clamp screw 40 rotates in a first direction to translate the inner shaft 30 in the proximal direction, the alignment location of the slots 105 and 205 moves proximally, thereby moving the anvil 100 toward the closed position with respect to the cartridge housing 200, and vice-versa when the clamp screw 40 is rotated in the opposite direction.

During clamping, the interaction between the inner shaft 30 and the slots 105 and 205 acts to press the proximal portions of the anvil 100 and the cartridge housing 200 away from each other. In this regard, the interface 300 between the convex surface 110 of the anvil 100 and the concave surface 210 of the cartridge housing 200 acts a fulcrum such that the distal clamping portions of the anvil 100 and the cartridge housing 200 are urged together.

Although the slots of the example clamping device 10 are positioned proximal to the axis of rotation of the anvil 100 with respect to the cartridge housing 200, it should be appreciated that the slots 105 and 205 may be position distal to the axis of rotation. In this situation, the interaction between the inner shaft and the slots would act to pull the anvil 100 toward the cartridge housing 200 at a location between the axis of rotation and the distal clamping portions of the anvil 100 and the cartridge housing 200.

The proximal ends of the actuation slots 105 of the anvil 100 are open. This allows the anvil 100 to be coupled and decoupled to and from the cartridge housing 200 in a simple and expeditious manner. To couple the anvil 100 to the cartridge housing 200, the open ends of the actuation slots 105 are aligned to receive the lateral extensions of the inner shaft 30. The anvil 100 is moved proximally so that the slots receive and slide along the axial extensions of the inner shaft 30 until the convex surface 110 of the anvil 100 is positioned below the concave surface 210 of the cartridge housing 200. The secondary positioning members 80 may then be inserted to extend into the secondary positioning slots 140.

To remove the anvil 100, the secondary positioning members 80 may be retracted and/or removed. The anvil 100 may then be pulled distally, allowing the convex surface 110 to clear the concave surface 210, until the lateral extensions of the inner shaft 30 exit the open proximal ends of the actuation slots 105.

As shown, e.g., in FIGS. 6 to 9, the proximal portion of the anvil 100 has two parallel, or substantially parallel, extensions or wings 150 into which the slots 205 are formed. The extensions 150 are separated by a medial space 160 that extends distally to a point beyond the convex surfaces 110. The protrusions 115 (along with convex surfaces 110) and the actuation slots 105 are formed or disposed on the medial or inner sides or faces of the extensions 150, while the secondary positioning slots 140 are formed or disposed on the outer sides or faces of the extensions 150.

The strength of the extensions 150 benefits from the presence of outer structure 151 adjacent to the blind slots 105, as opposed to through slots that would not have this structure 151. The strengthening due to this structure 151 may reduce the possibility of deflection and/or deformation of the extensions 150 under high clamping loads.

Figure 14:
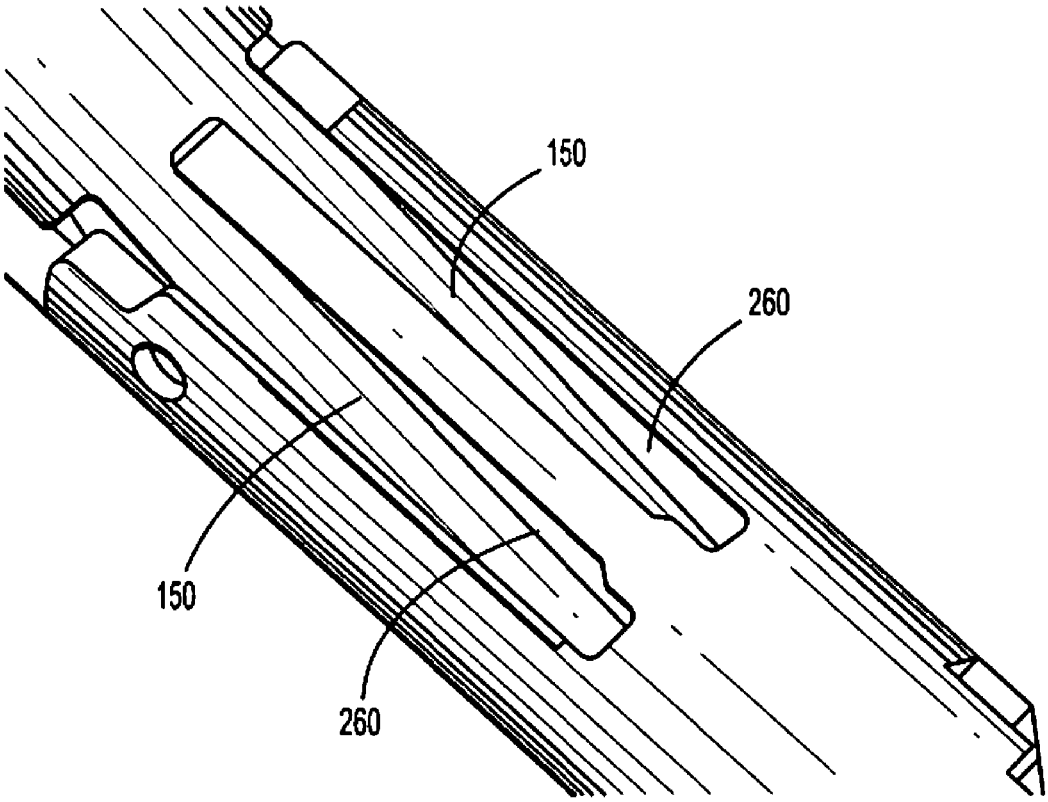
FIG. 14 shows a proximal portion of the clamping device.

When the anvil 100 is coupled to the cartridge housing 200 as described above, the extensions 150 are received in a pair of channels 260 of the cartridge housing 200, as shown, e.g., in FIG. 14. Thus, the extensions 150 of the anvil 100 are generally laterally captivated, confined or constrained in a particular arrangement by the cartridge housing 200. The channels 260 separate a middle extension 270 and two outer extensions 280. The middle extension 270 includes the slot 205, and the concave surfaces 210, while the outer extensions 280 include the secondary positioning apertures 240. The middle extension 270 also includes first and second axial apertures 290 and 291, which extend axially, referring to FIG. 5a, through the middle extension 270 to corresponding proximal openings in the middle extension 270. The first axial aperture 290 allows the firing shaft 50, which is housed in an enclosed channel or bore 292 of the middle extension 270, to access and drive a cutting and staple-driving element in the distal portion of the cartridge housing 200. The second aperture 291 provides access to an enclosed channel or bore 293 between the distal and proximal ends of the middle extension 270. The channel 293 may be used for any appropriate purpose, including, e.g., providing a housing for wiring, which may be used, e.g., to communicate information related to staple cartridges that may be housed in the cartridge housing 200. The information may be, e.g., stored on a chip of the staple cartridge. The distal portion of the cartridge housing 200, which functions as a lower clamping jaw, includes a channel 275 configured to receive the staple cartridge.

The lateral confinement, captivation or constraint of the extensions 160 of the anvil 100 may serve to prevent or reduce the likelihood of lateral deflection and/or deformation of the extensions 160, e.g., under high clamping forces.

Further, the structure of the extensions 270 and 280 of the cartridge housing 200 may prevent or reduce the likelihood of deflection and/or deformation of the cartridge housing 200. In this regard, the extensions 270 and 280 extend in the plane of the clamping rotation of the anvil with respect to the cartridge housing. This may provide added strength in the plane of the clamping rotation of the anvil 100 with respect to the cartridge housing 200. Further, the presence of substantial structure due to the outer extensions 280 at a distance (e.g., along the lateral circumference of the cartridge housing 200) from the axial centerline of the cartridge housing 200 may provide increased torsional rigidity to further resist deflection of the cartridge housing 200.

The cartridge housing 200 includes lateral supports or ribs 271, 272 that extend between the middle extension 270 and the outer extensions 280. The lateral supports 271, 272 are spaced and dimensioned to avoid interfering with the rotation of the wings or extensions 150 of the anvil 100 when the anvil 100 is rotated during clamping and opening procedures.

Figure 15:
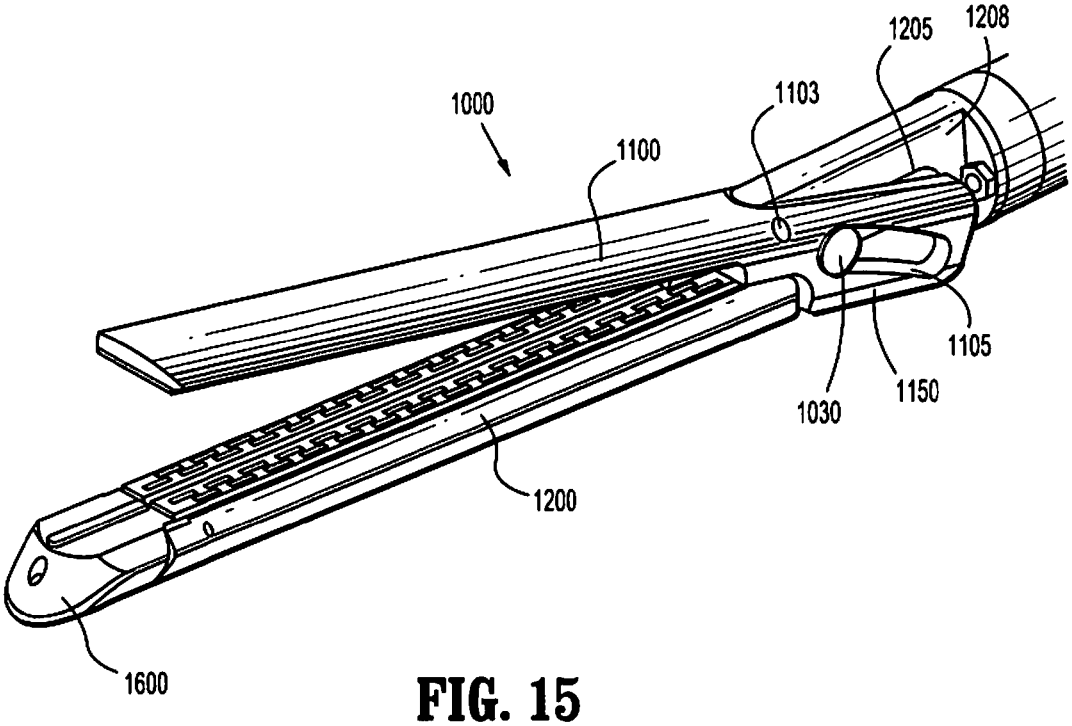
FIG. 15 shows an alternative clamping device.

FIG. 15 illustrates an alternative clamping device 1000. The device 1000 includes a first jaw or anvil 1100 and a second jaw or staple cartridge housing 1200. The staple cartridge housing 1200 is shown with a staple cartridge 1600, which is of a type also insertable into the staple cartridge housing 200 described above. The anvil 1100 is rotatable with respect to the cartridge housing 1200 about a pin inserted through a bore 1103 of the anvil 1100 and a corresponding bore of the cartridge housing 1200. The anvil 1100 is actuatable between an open state and a closed state via actuation of a shaft 1030 along a slot 1205 of the cartridge housing 1200 and a pair of slots 1105 of the anvil.

The slots 1105 are formed in two respective wings or extensions 1150 of the anvil 1100. As opposed to the slots 105 disposed in the extensions 150 of the anvil 100, the slots 1105 are through-slots, extending entirely through the structure of each respective extension 1150. Thus, under high clamping forces applied between the anvil 1100 and the cartridge housing 1200, the extensions 1150 may be more likely to deflect and/or deform. Moreover, the bore 1103, which forms a through hole in the anvil 1100, may further reduce the clamping forces that may be applied without deflection or deformation in the anvil 1100 and/or the cartridge housing 1200, as opposed to the interface 300 of the clamping device 10.

Further, the clamping device 1000 does not include any structure disposed laterally (along the axis of rotation) outside of the extensions 1150. Thus, under high clamping forces, the extensions 1150 have less constraint against laterally outward deflection, as compared to the clamping device 10, where the outer extensions 280 of the cartridge housing 200 extend along laterally outward sides of the extensions 150 of the anvil 100 to generally laterally confine in a particular arrangement the extensions 150.

Still further, since the only structure of the cartridge housing 1200 extending along the axial extension of the slot 1205 is a single vertically oriented axial extension 1208, the cartridge housing 1200 may be more susceptible to deflection, as opposed to the cartridge housing 200, which has the additional structural support provided by the two outer extensions 280. With regard to the clamping device 1000, it is noted that the stresses due to the clamping forces exerted between the distal portions of the anvil 1100 and the cartridge housing 1200 are concentrated in the interface between the distal or jaw portion and the single extension 1208. In contrast, referring to the clamping device 10 illustrated, e.g., in FIGS. 11 and 12, the interface between the distal or jaw portion of the cartridge housing 200 is spread among the two outer extensions 280 and the middle extension 270. This may allow greater clamping forces to be applied without unacceptable deflection or fatigue failure at the junction between the distal jaw portion and the proximal portion of the cartridge housing 200.

Figure 16:
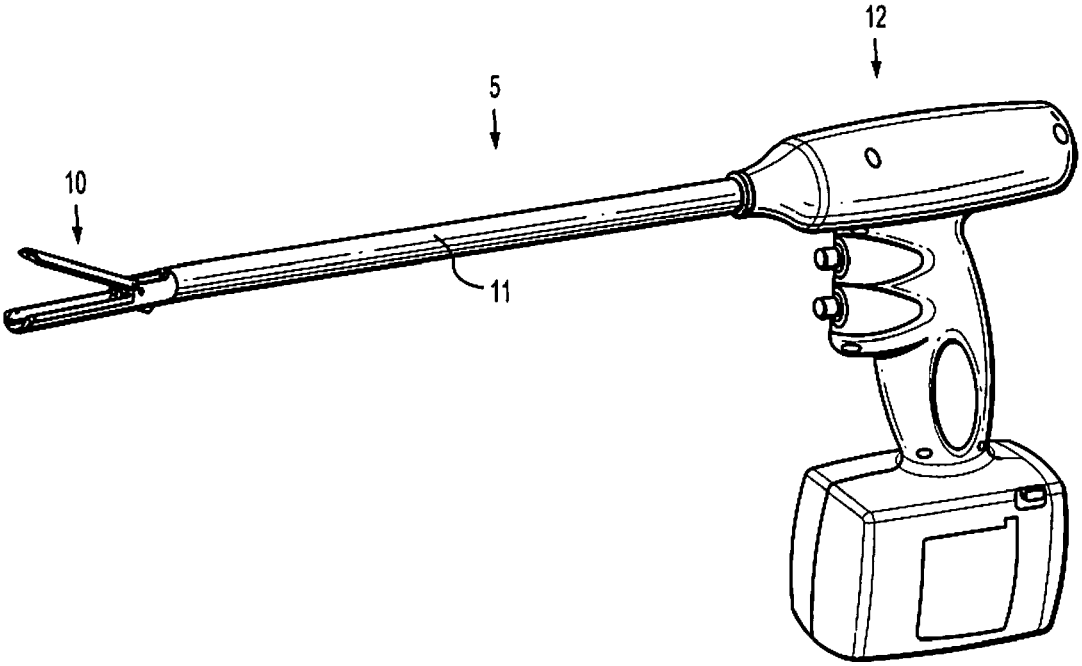
FIG. 16 shows a surgical instrument having the clamping device of FIGS. 1 to 14.

FIG. 16 shows a surgical instrument 5 including the clamping device 10. The clamping device 10 is coupled to a shaft housing 11, that contains a first drive shaft configured to drive clamp screw 40 and a second drive shaft configured to drive bevel gear shaft 60. At a proximal end of the shaft housing 11 is a handle portion 12 that includes user controls and at least one actuator configured to rotate the first and second drive shafts based on the user controls. In this regard, the drive shafts are independently rotatable so that the clamping (or opening) of the jaws may be controlled independently from the driving of the cutter/staple pusher. The instrument contains many features that are analogous to the instruments described in U.S. Patent Application Publication No. 2009/0101692, which is expressly incorporated herein in its entirely by reference thereto. Although the example instrument 5 is a hand-held, self-contained, battery-powered unit, it should be appreciated that the clamping device 10 may be provided with any appropriate instrument, e.g., a console-based surgical instrument.

Figure 17:
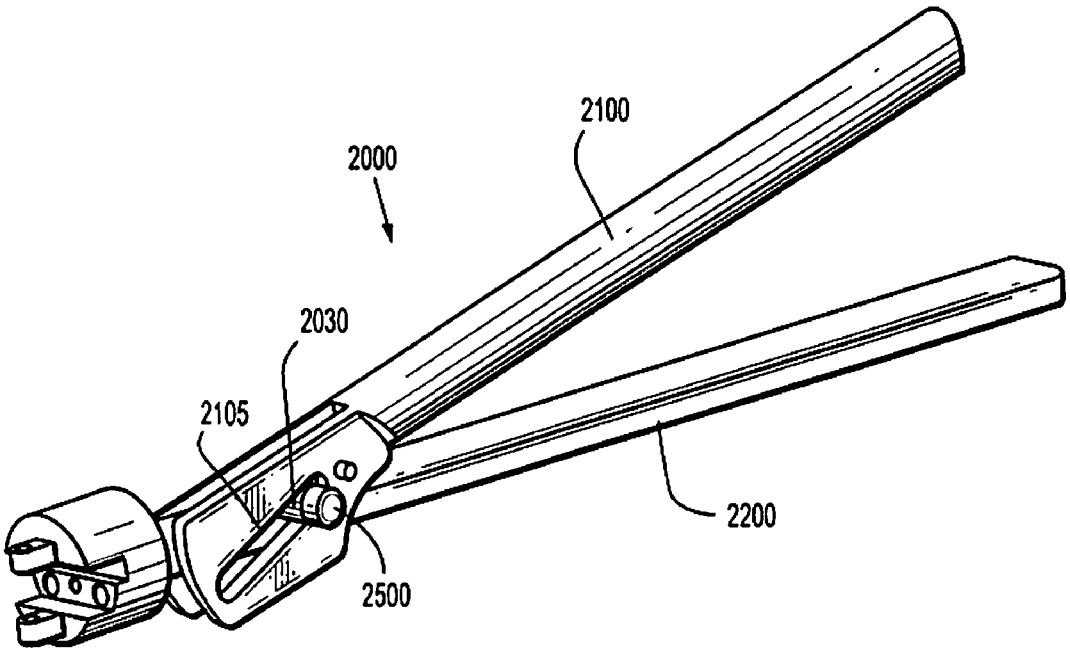
FIG. 17 shows a clamping device according to an example embodiment of the present invention.
Figure 18:
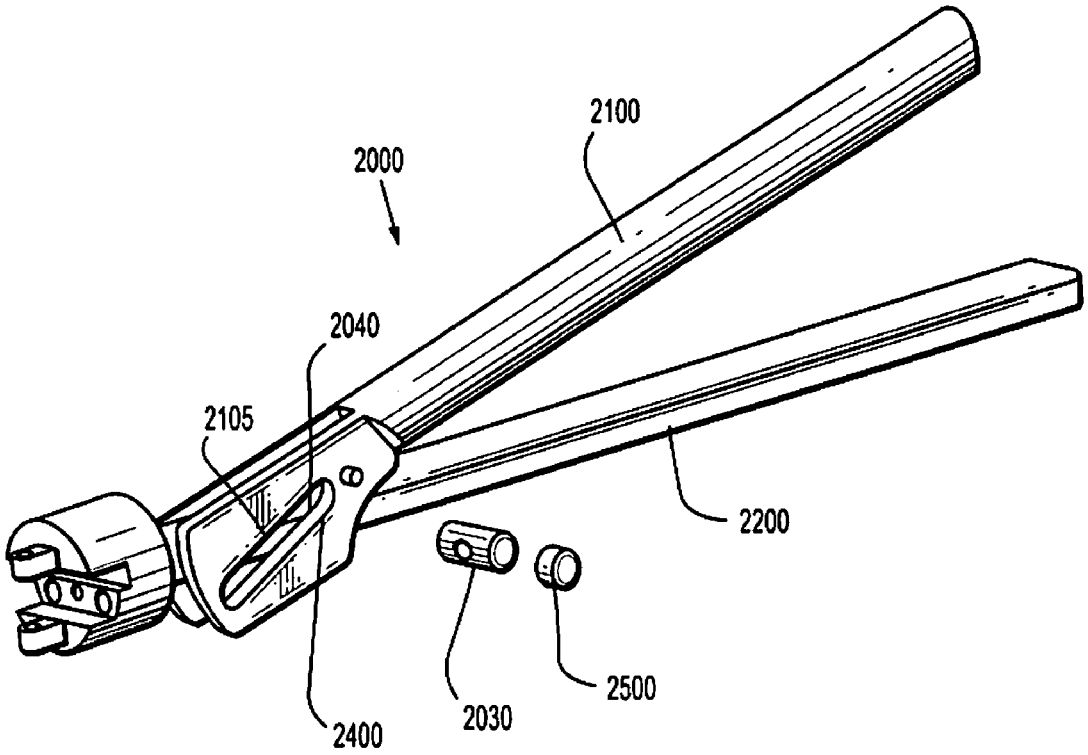
FIG. 18 is an exploded view of the clamping device of FIG. 17.

FIGS. 17 and 18 show a clamping device 2000. The clamping device 2000 includes the features of the clamping devices described above, but differs in that the anvil 2100 includes through slots 2105 rather than blind slots 105. This arrangement may be suitable to simplify the manufacturing of the slots.

Since the through slots 2105 do not have open proximal ends, such as those of blind slots 105, the clamping device is not assembled in exactly the same manner as described above with regard to clamping device 10. This is because the closed distal end of the through slots 2105 prevent the anvil 2100 from being proximally slid onto the inner shaft 2030. Thus, the anvil 2100 is rotatably coupled to the housing 2200 prior to placement of the inner shaft 2030. In this regard, after the anvil 2100 is coupled to the housing 2200, the through slot 2105 of the anvil 2100 is aligned with a hole or aperture 2400 in the side of the housing 2200. At this stage, the inner shaft 2030 may be inserted through the hole 2400 until the inner shaft 2030 engages both through slots 2105. The clamp screw 2040 may then by inserted to engage the inner threads of the inner shaft 2030.

To reduce any possibility of contamination, e.g., dirt, entering the mechanism through the hole 2400, a plug 2500 is provided, which closes the hole after the inner shaft 2030 has been inserted therethrough. Although the clamping device 2000 has a single hole with a single plug, it should be understood that two or more holes and/or two or more plugs may be provided. However, it may be suitable to minimized the number of holes to limit the possibility of contamination, simplify the manufacturing process, and/or reduce any possibility of compromising the strength of the housing 2200.

Although the through slots 2105 are shown as enclosed, it should be understood that the through slots 2105 may have a forked structure, such that one end of one or more of the slots 2105, e.g., a proximal end, is open.

Although the present invention has been described with reference to particular examples and exemplary embodiments, it should be understood that the foregoing description is in no manner limiting. Moreover, the features described herein may be used in any combination.

What is claimed is:

1. A device for clamping tissue, comprising:

a first jaw including:

a distal portion adapted to communicate with tissue, and a proximal portion having a first wing and a second wing, *wherein the first wing includes a first blind slot and the second wing includes a second blind slot, the first and second blind slots configured to receive opposite ends of an actuation shaft*; and a second jaw including:

a distal portion adapted to communicate with tissue, and a proximal portion having a first slot and a second slot, the first slot disposed between a middle structure and a first lateral structure, the second slot disposed between the middle structure and a second lateral structure, wherein the first jaw is rotatably coupleable to the second jaw with the first wing extending into the first slot and the second wing extending into the second slot.

[2. The device of claim 1, wherein the first wing includes a first blind slot and the second wing includes a second blind slot, the first and second blind slots configured to receive opposite ends of an actuation shaft.]

3. The device of claim [2] *1*, wherein the middle structure of the second jaw includes a slot configured to receive a middle portion of the actuation shaft when the ends of the actuation shaft are received in the blind slots of the first and second wings.

4. The device of claim 1, wherein the first jaw includes a first bearing surface formed monolithically with the first jaw and the second jaw includes a second bearing surface formed monolithically with the second jaw, the first bearing surface communicating with the second bearing surface to define an axis of rotation between the first jaw and the second jaw when the first jaw is rotatably coupled to the second jaw.

5. The device of claim 4, wherein the first and second bearing surfaces have curvatures that maintain an axial position of the first jaw with respect to the second jaw when a clamping force is applied between the first jaw and the second jaw.

6. The device of claim 4, further comprising a positioning member coupled to one of the first jaw and the second jaw and configured to prevent removal of the first jaw from the second jaw and to allow rotation of the first jaw with respect to the second jaw.

7. The device of claim 6, wherein the positioning member is at least one of a pin and a screw.

8. The device of claim 6, wherein the positioning member is configured to extend from the one of the first jaw and the second jaw into a curved slot of the other one of the first jaw and the second jaw.

9. The device of claim 8, wherein the curved slot is a blind slot.

10. The device of claim 1, wherein the first jaw is an anvil and the second jaw is a staple cartridge housing configured to drive staples into the anvil when the anvil is in a closed position.

11. A device for clamping tissue, comprising:

a first jaw including:

a first jaw body having a proximal portion and a distal clamping portion[, and]*;* a first bearing surface formed monolithically with the first jaw body as a single piece; *and*

*a first wing and a second wing, wherein the first wing includes a first blind slot and the second wing includes a second blind slot;* a second jaw including:

a second jaw body having a proximal portion and a distal clamping portion, and a second bearing surface formed monolithically with the second jaw body, the second jaw being rotatably coupleable to the first jaw such that the first bearing surface communicates with the second bearing surface at an interface; and a driver configured to rotate the first jaw with respect to the second jaw with the interface acting as a fulcrum and defining an axis of rotation between the first jaw and the second jaw*, wherein the driver includes a shaft configured to extend into each of the first blind slot and the second blind slot*.

12. The device of claim 11, wherein the first bearing surface and the second bearing surface are configured to slide with respect to each other along the interface when the driver rotates the first jaw with respect to the second jaw.

13. The device of claim 12, wherein the interface extends along a circular arc, the first jaw rotatable with respect to the second jaw about an axis of rotation corresponding to the circle center of the circular arc.

14. The device of claim 11, wherein the first bearing surface is formed in the first jaw without extending entirely through the first jaw and the second bearing surface is formed in the second jaw without extending entirely through the second jaw.

[15. The device of claim 11, wherein the first jaw includes a first wing and a second wing, the first wing including a first blind slot and the second wing including a second blind slot.]

[16. The device of claim 15, wherein the driver includes a shaft configured to extend into each of the first blind slot and the second blind slot.]

17. The device of claim [16] *11*, wherein the shaft is actuatable along a slot in the second jaw to rotate the first jaw with respect to the second jaw.

18. The device of claim 17, wherein the shaft is disposed proximally with respect to the interface between the first bearing surface and the second bearing surface.

19. The device of claim 11, wherein the first jaw is axially insertable and removable from the second jaw when no clamping force is applied between the first jaw and the second jaw.

20. The device of claim 19, further comprising a positioning member coupled to one of the first jaw and the second jaw and configured to prevent axial removal of the first jaw from the second jaw and to permit rotation of the first jaw with respect to the second jaw.

21. The device of claim 20, wherein the positioning member is configured to limit the range of rotation between the first jaw and the second jaw to a predetermined angular range.

22. The device of claim 20, wherein the positioning member is configured to extend from the one of the first jaw and the second jaw into a curved slot of the other one of the first jaw and the second jaw.

23. The device of claim 22, wherein the curved slot is a blind slot.

* * * * *